(12) United States Patent
Hammerstedt et al.

(10) Patent No.: US 7,422,726 B2
(45) Date of Patent: Sep. 9, 2008

(54) INTEGRATED CONTAINER FOR LYOPHILIZATION, REHYDRATION AND PROCESSING OF BIOLOGICAL MATERIALS

(75) Inventors: Roy H. Hammerstedt, Boalsburg, PA (US); Stephen S. Schwartz, State College, PA (US)

(73) Assignee: Blood Cell Storage, Inc., Seattle, WA (US)

( * ) Notice: Subject to any disclaimer, the term of this patent is extended or adjusted under 35 U.S.C. 154(b) by 368 days.

(21) Appl. No.: 10/278,711

(22) Filed: Oct. 23, 2002

(65) Prior Publication Data

US 2004/0081588 A1    Apr. 29, 2004

(51) Int. Cl.
*F26B 5/06* (2006.01)
(52) U.S. Cl. .................. 422/101; 422/102; 34/284; 34/287; 426/384
(58) Field of Classification Search ............ 422/101, 422/102; 426/384; 34/284, 287
See application file for complete search history.

(56) References Cited

U.S. PATENT DOCUMENTS 3,574,950 A * 4/1971 Dantoni ..................... 34/92
4,973,327 A * 11/1990 Goodrich et al. ........... 604/408
6,517,526 B1 * 2/2003 Tamari ...................... 604/403

OTHER PUBLICATIONS http://en.wikipedia.org/wiki/polypropylene.*

* cited by examiner

*Primary Examiner*—Jill Warden
*Assistant Examiner*—Paul S Hyun

(57) ABSTRACT

An apparatus to lyophilize, store, transport, rehydrate, and process aqueous biological materials in a container which maintains sterility of its contents, allows container shrinkage after lyophilization, and optimally permits filtration or dialysis of the contents in situ, without the need for a second or series of additional containers. These benefits are met by a microporous container constructed of a membrane that is water vapor permeable, yet water impermeable.

7 Claims, 6 Drawing Sheets

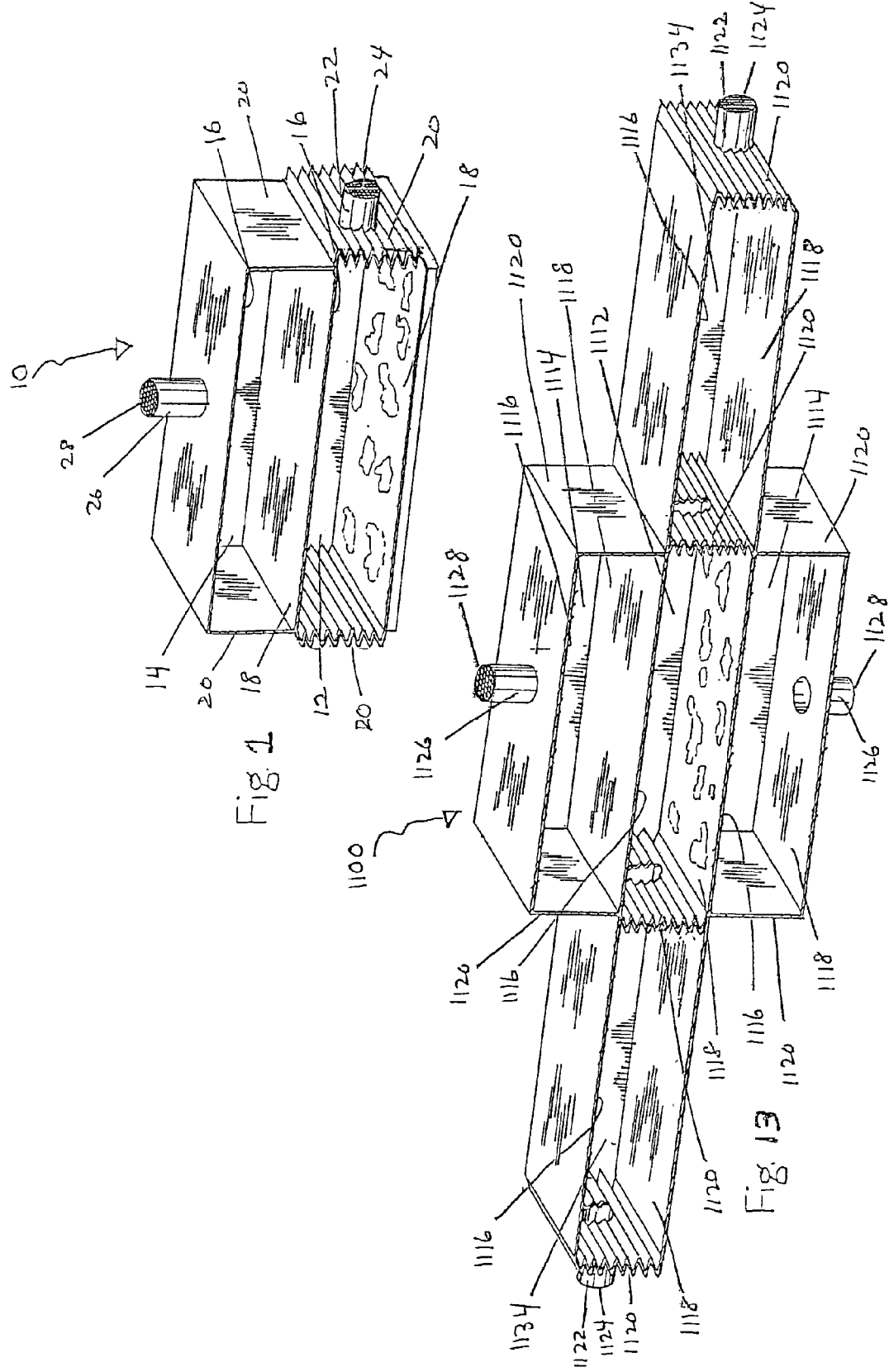

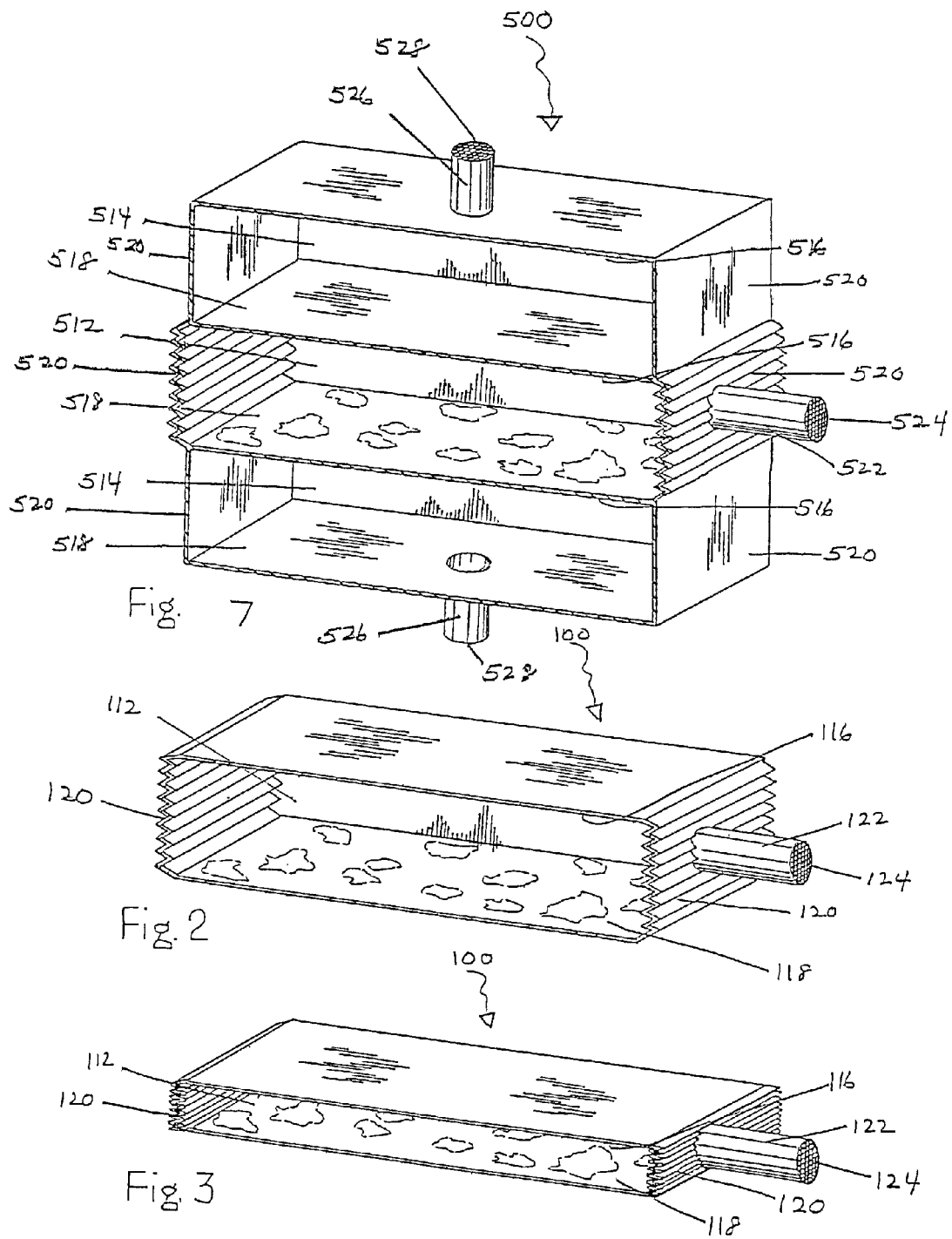

INTEGRATED CONTAINER FOR LYOPHILIZATION, REHYDRATION AND PROCESSING OF BIOLOGICAL MATERIALS

BACKGROUND OF THE INVENTION

1. Field of the Invention

The invention relates to the use of an integrated container for lyophilization, storage, distribution, and processing of fluids, cells or tissues.

2. Description of Related Art

Distribution of materials requires storage under conditions suitable for optimum product stabilization, minimum storage cost, and simple operation at site of use. This is of particular importance in the field of biopharmaceuticals because of the propensity of such products to lose their biological activity in the liquid, aqueous state. Cooling below −20 degrees Celsius (° C.) is a popular approach, but costs of maintaining the materials at reduced temperatures (−20°, −80° or −196° (C.)) for extended periods and during transport are high. Additionally, many important biological products, such as blood and plasma, have high mass (weight), which in turn creates the shipping challenges of logistics and expense.

A typical example of a biological material susceptible to the above challenges is blood plasma. With whole blood having a limited storage life, blood plasma and its ability to keep for two years (either frozen or lyophilized) has long been an important medical product, particularly in hospitals and military operations. Transporting blood plasma per se is problematic due to the need for temperature controls and due to the high mass of its primary constituent, water. Even when blood plasma is lyophilized to remove the water and its attendant disadvantages, storage, transport and processing for use become no easier because the container is fixed prior to lyophilization and because of the documentation and rehydration requirements of such products.

Lyophilization is a useful mode of storing many biological products, and involves the processes of freezing, removal of water as vapor (under a vacuum), storage, and rehydration prior to use. Existing methods for lyophilizing aqueous biological materials depend upon the use of a rigid container, which can withstand the vacuum imposed within the container to sublimate the water for removal as water vapor. The water vapor is removed via a connection to the neck of the container, with storage and shipment resulting in large amounts of wasted space, namely, the space formerly occupied by the water. If further processing is required after hydration with pyrogen-free water, such as removal of certain constituents by filtration or dialysis, the product must be transferred to a new container. Aseptic conditions are essential, but many manipulative steps can compromise sterility.

Some examples of materials that undergo such processing include: vaccines; extracts from animal, vegetable, bacterial, yeast sources; proteins and carbohydrates sensitive to heat; oligonucleotides; organometallics; liposomes; antibiotics; and blood products. In such applications, during the manufacturing process, the products are lyophilized for later rehydration as needed. Additional applications in genetic engineering, biochemistry, biotechnology, cell biology, and medicine include storage of bacterial, mammalian, yeast, and plant cells. In such situations, a "cryostabilizing" agent, such as mannitol or trehalose, is added to the cell suspension before freezing. After storage and rehydration, these agents should be removed before the cells can be used for direct therapeutic application.

Cost-effective lyophilization requires a confined container that does not hinder the processing of the biological material. At a minimum, such processing requires: a simple means of applying a vacuum to the frozen solution; the use of a container with mechanically strong walls to withstand the pressures created during the vacuum; provision of a maximum surface to volume ratio for the frozen materials in order to facilitate egress of water vapor from the frozen matrix; and simple removal of the product when needed. Both rigid bottles and pliable bags for storage of fluids and cells are widely used, often featuring compartments separated by a common wall. Common wall materials available for such units range in their water vapor permeability from zero to high permeability.

One common lyophilization approach involves "shell freezing" materials within wide mouth glass flasks that are attached to a vacuum system. The water vapor exits from the mouth by sublimation and when completed, the vacuum is released and the flask is sealed and removed for storage. The disadvantages of this approach include the large size of the container to be stored, the fragility of the glass container, and the difficulty of maintaining aseptic conditions during the process.

W.L. Gore & Associates recently introduced a system that addresses many of these disadvantages (Genetic Engineering News 22: pp. 22 and 26, Jan. 1, 2002). Their approach involves the use of a disposable lightweight tray composed of a filling port on one of five rigid walls with a permeable Gore-Tex® expanded polyytetrafluoroethylene (ePTEE) laminate developed for this process. The laminate material has a microporous "body" to which a large mesh cover is attached for structural stability. The material was designed to provide a high vapor transfer rate and integrity to prevent passage of microorganisms, such as *Bacillus subtillis* and *Bacillus licheniformis*. The process involves filling of the container with the material to be lyophilized by freezing, placing the tray into a vacuum chamber, transferring of the water through the ePTEE membrane, returning the container to atmospheric conditions, and removing of the tray from the vacuum chamber for storage.

Despite the advances accorded by this approach, several critical features either have not been addressed or have been specifically excluded. First, containers are not provided in a sterile condition but contain specific instructions that any such sterilization is the sole responsibility of the user. Steam sterilization can be used, if necessary, but other useful procedures are either not recommended (e.g., radiation techniques) or are not addressed (e.g., ethylene oxide, gas plasma, formaldehyde gas, hydrogen peroxide vapor). Second, after removal of the water, the container is returned to the atmosphere, and the product cannot be stored under a vacuum due to the "open" nature of the ePTEE materials. This allows interaction of the lyophilized materials with oxygen and atmospheric water vapor during storage. Third, the ePTEE surface must be sealed with a foil barrier pouch or other vapor barrier enclosure to prevent product rehydration. This requires additional post-processing steps. Fourth, the rigid nature of the tray system precludes the integration and use of such a system into processes that involve centrifugation and decantation of fluids and cell suspensions (e.g., blood cell fractionation). Finally, the approach does not allow for facile exchange of the solution after lyophilization (e.g., removal of mannitol). This precludes the use of a single package for the storage and delivery of cells by infusion.

Accordingly, a need remains for a lyophilization method and apparatus that overcomes the prior art problems of wasted storage space, potential compromise of sterility, and multiple method steps in more than one container.

SUMMARY OF THE INVENTION

The present invention is an apparatus to lyophilize, store, transport, rehydrate, and process aqueous biological materials in a container which maintains sterility of its contents, allows container shrinkage after lyophilization, and optimally permits filtration or dialysis of the contents in situ, without the need for a second or series of additional containers. These benefits are met by a microporous container constructed of a membrane that is water vapor permeable, yet water impermeable.

BRIEF DESCRIPTION OF THE DRAWINGS

FIG. 1 is a top perspective view, partially in section, of an integrated container for lyophilization and rehydration in accordance with the present invention;

FIG. 2 is a top perspective view, partially in section, of a collapsible container with a lyophilization compartment subcomponent made in accordance with the present invention;

FIG. 3 is a top perspective view, partially in section, of the embodiment shown in FIG. 2 in a collapsed state;

FIG. 7 is a top perspective view, partially in section, of another embodiment of the present invention;

FIG. 13 is a top perspective view, partially in section, of a further embodiment of the present invention.

DESCRIPTION OF THE PREFERRED EMBODIMENTS

Figure 12:
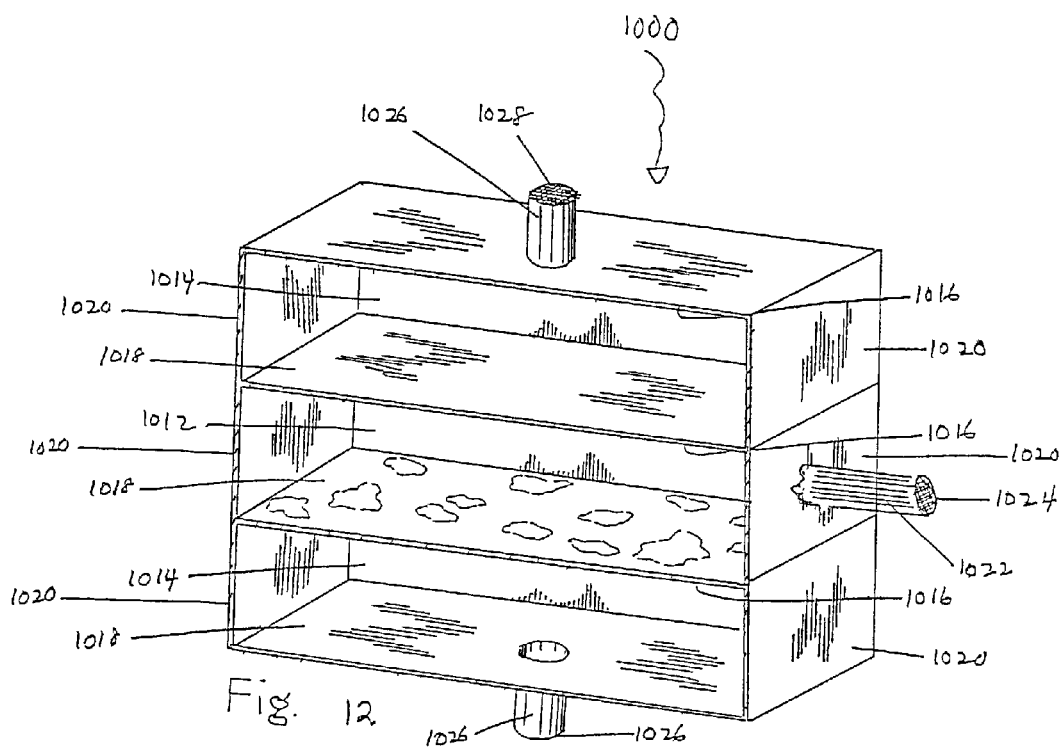
FIG. 12 is a top perspective view, partially in section, of another embodiment of the present invention.

The present invention is a container having a lyophilization compartment and one or more vacuum-processing compartments. The common wall between the lyophilization compartment and one adjacent vacuum-processing compartment is fabricated with a flexible controlled pore membrane with hydrophobic surfaces that is water vapor permeable, yet water impermeable, with the remaining walls of the container fabricated with a pliable material capable of compression upon vacuum pressure and of maintaining a barrier between an internal vacuum and the external atmosphere. The lyophilization compartment contains an access port to allow entry of biological materials or water. Each vacuum-processing compartment contains an exit port that connects to a vacuum and condenser system (not shown). All ports contain a barrier therein to maintain sterility of the material being processed. Mechanical strength sufficient to retain the compartments from collapse under vacuum pressure can be achieved either by external or internal mechanical restraints. External mechanical restraints are located on the external surfaces of the container and are attached to tabs located on the external surfaces of the container. Internal mechanical restraints are located between the lyophilization compartment and the vacuum-processing compartment and can be made of either a thin honeycomb-like, open cell plastic structure that lies adjacent to the pore membrane, or a pattern of crisscrossing raised plastic "bumps" that are placed on top of the pore membrane.

One way to address some of the disadvantages of the prior art is to use membranes of any material that meet the requirements for sterility and selective permeate flow (gas permeable, yet water impermeable). An example of such a material is RoTrac® Capillary Pore Membranes provided by Oxyphen AG. These membranes are made of a polyester film that is exposed to a controlled beam of heavy ions, such as krypton. When the accelerated ions pass through the polymer film, they break the polymer chains and the tracks are accessible for chemical etching. The cylindrical pores that are formed can have a diameter between 0.03 µm and 10 µm, with the number of pores per unit area adapted to the requirements of the particular system. The separation membrane can then be laminated to various non-woven materials that differ according to their water-attractant characteristics (e.g., polypropylene that is hydrophobic; polyester-terephtalate that is hydrophilic), in order to achieve mechanical stability. The pores of the support material are much larger than the membrane pores in order to allow unhindered permeate flow. The resultant laminate membrane can be sterilized several times, without shrinking, using a variety of sterilization methods, including autoclave, steam-sterilization, formaldehyde, hydrogen peroxide, percarbonic acid, ethylene oxide, or gamma radiation. Biological materials differ widely in their capacity to tolerate "residual" materials incident to sterilization, thus emphasizing the need for use of such membranes that are capable of sterilization by a variety of methods.

RoTrac® Capillary Pore Membranes differ from other microfiltration membranes in several critical ways. Most membranes have a layer with an irregular spongeous structure that does not define an exact pore diameter. However, RoTrac® Capillary Pore Membranes have a well-defined geometry, i.e., a known pore size (diameter) with a diameter tolerance of a maximum 10%, and a defined number of pores per unit area. They have a high porosity, homogeneous area density and defined pore diameter, and are highly gas permeable. The unique properties of these membranes allow simple incorporation into customized membrane products by direct injection molding, ultrasonic welding, heat, or use of adhesives, thus making them suitable for biomedical applications, although they have had, to date, limited biomedical use.

Referring now to FIG. 1, the container 10 is a semi-collapsible closed structure having a cavity therein. The cavity is divided equally into two compartments: a lyophilization compartment 12 and vacuum-processing compartment 14. Each compartment 12, 14 is bounded by six walls comprised of an upper face 16, a lower face 18, and four lateral faces 20. Although the four lateral faces 20 may be pleated, they could also be flat, yet flexible enough to collapse. Also it is possible that the two walls are straight lateral faces 20, while opposite lateral faces 20 are pleated. The upper face 16 of the lyophilization compartment 12 is fabricated entirely or in part with a flexible controlled pore membrane with hydrophobic surfaces, and the four lateral faces 20 are fabricated with a flexible material that is capable of compression under vacuum pressure and of maintaining a barrier between an internal vacuum and the external atmosphere. Examples of materials that provide both flexibility and resistance to vacuum pressure are plastics, such as polyethylene, polyurethane and polyester/polyether block copolymers. An access port 22 is located on a lateral face 20 of the lyophilization compartment 12. The access port 22 allows for the entrance of biological materials or water therein. The access port 22 is sealed with a microporous hydrophobic membrane barrier 24 to maintain sterility. The upper face 16 of the lyophilization compartment 12 and the lower face 18 of the vacuum-processing compartment 14 serve as a common wall between the lyophilization compartment 12 and the vacuum-processing compartment 14. The upper face 16 and lateral faces 20 of the vacuum-processing compartment 14 and the lower face 18 of the lyophilization compartment 12 are fabricated with a rigid material, such as acrylic, polycarbonate, polypropylene or ABS. The vacuum-processing compartment 14 contains an exit port 26 therein that is sealed with a barrier 28 to maintain sterility. The exit port 26 is connected to a vacuum and condenser system (not shown), commonly known and used by those skilled in the art, for removal of water vapor from the lyophilization compartment 12. During compression of the lyophilization compartment 12, the vacuum can be replaced by inert gases according to the needs of the user. An additional feature of the container 10 is the versatility of the lyophilization compartment 12, allowing it to serve as a subcomponent of a more complex system, such as for blood fractionation. Furthermore, the entire container 10 can be sterilized before use.

FIG. 2 is an embodiment of a collapsible container 100 with a lyophilization compartment subcomponent that can be used in a pre-existing vacuum-processing system. The container 100 is composed of a lyophilization compartment 112 bounded by six walls comprised of an upper face 116, a lower face 118, and four lateral faces 120. The upper face 116 of the lyophilization compartment 112 is fabricated entirely or in part with a flexible controlled pore membrane with hydrophobic surfaces, and the four lateral faces 120 are fabricated with a flexible material that is capable of compression under vacuum pressure and of maintaining a barrier between an internal vacuum and the external atmosphere. An access port 122 is located on a lateral face 120 of the lyophilization compartment 112. The access port 122 is sealed with a microporous hydrophobic membrane barrier 124 to maintain sterility.

FIG. 3 illustrates the collapsible container 100 with a lyophilization compartment subcomponent in its collapsed state after completion of vacuum processing.

Figure 4:
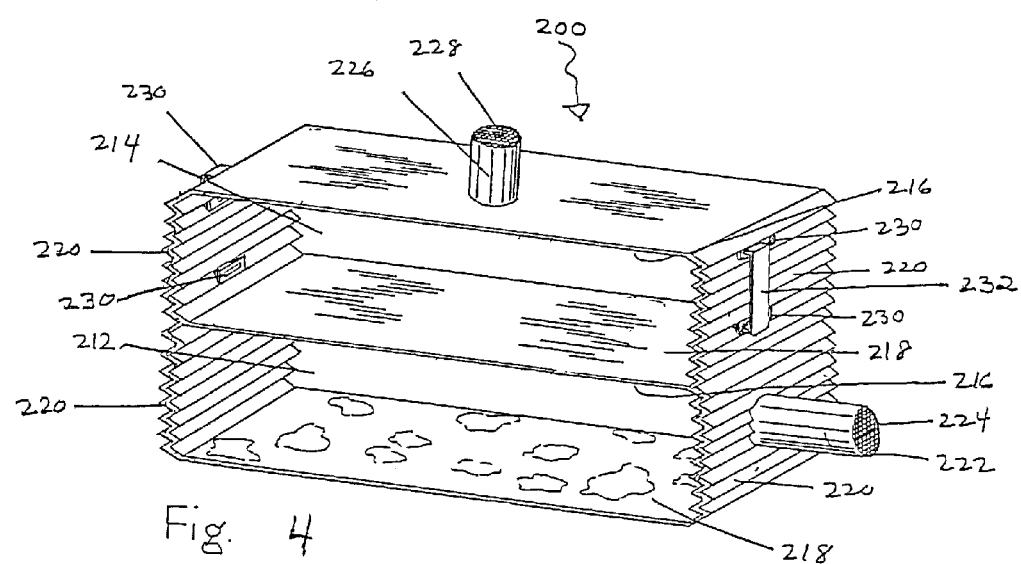
FIG. 4 is a top perspective view, partially in section, of another embodiment of the present invention.

FIG. 4 is an embodiment of a fully collapsible container 200, in which the cavity therein is divided into two compartments: a lyophilization compartment 212 and a vacuum-processing compartment 214. Each compartment 212, 214 is bounded by six walls comprised of an upper face 216, a lower face 218, and four lateral faces 220. The upper face 216 of the lyophilization compartment 212 is fabricated entirely or in part with a flexible controlled pore membrane with hydrophobic surfaces, and the four lateral faces 220 are fabricated with a flexible material that is capable of compression under vacuum pressure and of maintaining a barrier between an internal vacuum and the external atmosphere. An access port 222 is located on a lateral face 220 of the lyophilization compartment 212. The access port 222 is sealed with a microporous hydrophobic membrane barrier 224 to maintain sterility. The upper face 216 of the lyophilization compartment 212 and the lower face 218 of the vacuum-processing compartment 214 serve as a common wall between the lyophilization compartment 212 and the vacuum-processing compartment 214. The upper face 216 of the vacuum-processing compartment 214 and the lower face 218 of the lyophilization compartment 212 are fabricated with a rigid material as described above. The lateral faces 220 of the vacuum-processing compartment 214 are fabricated with a flexible material as described above. The vacuum-processing compartment 214 contains an exit port 226 therein and is sealed with a barrier 228 to maintain sterility. In order to provide mechanical strength sufficient to retain the vacuum-processing compartment 214 from collapse under the vacuum pressure, the outside of each lateral face 220 of the vacuum-processing compartment 214 has a tabular structure 230 affixed thereto capable of attaching reversibly to an external mechanical restraint 232. After lyophilization, the external mechanical restraints 232 can be released, allowing the container 200 to compress to a minimal volume for storage or transport.

Two alternatives to external restraints 232, described above, are to use internal restraints that are capable of providing mechanical strength sufficient to prevent the upper face 216 of the vacuum-processing compartment 214 from coming in contact with the flexible controlled pore membrane of the lyophilization compartment 212.

Figure 5:
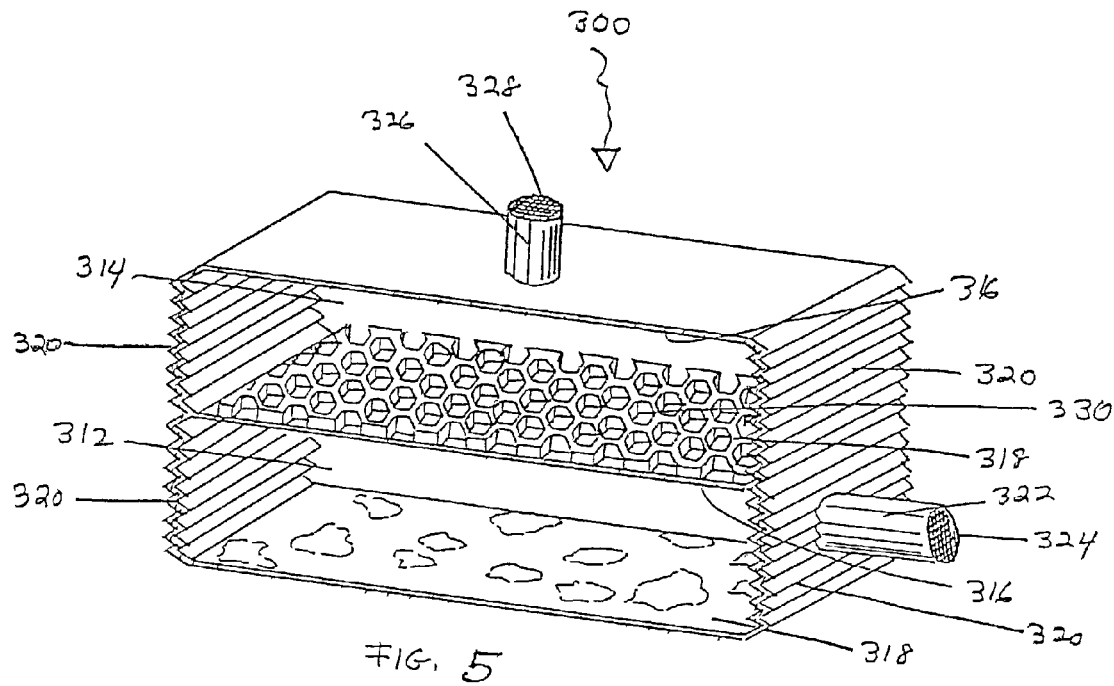
FIG. 5 is a top perspective view, partially in section, of another embodiment of the present invention.

FIG. 5 is an embodiment of a fully collapsible closed container 300 that uses an internal honeycomb-like open cell plastic structure to prevent contact between the upper face 316 and the lower face 318 of the vacuum-processing compartment 314. The mesh shape need not be honeycomb-like but can have any mesh configuration. The collapsible closed container 300 contains a cavity therein divided into two compartments: a lyophilization compartment 312 and a vacuum-processing compartment 314. Each compartment 312, 314 is bounded by six walls comprised of an upper face 316, a lower face 318, and four lateral faces 320. The upper face 316 of the lyophilization compartment 312 is fabricated entirely or in part with a flexible controlled pore membrane with hydrophobic surfaces, and the four lateral faces 320 are fabricated with a flexible material that is capable of compression under vacuum pressure and of maintaining a barrier between an internal vacuum and the external atmosphere. An access port 322 is located on a lateral face 320 of the lyophilization compartment 312 and is sealed with a microporous hydrophobic membrane barrier 324 to maintain sterility. The upper face 316 of the lyophilization compartment 312 and the lower face 318 of the vacuum-processing compartment 314 serve as a common wall between the lyophilization compartment 312 and the vacuum-processing compartment 314. The upper face 316 of the vacuum-processing compartment 314 and the lower face 318 of the lyophilization compartment 312 are fabricated with a rigid material as described above. The lateral faces 320 of the vacuum-processing compartment 314 are fabricated with a flexible material as described above. The vacuum-processing compartment 314 contains an exit port 326 therein and is sealed with a barrier 328 to maintain sterility. An internal restraint 330, fabricated from a honeycomb-like open cell plastic structure, is attached to the lower face 318 of the first distal vacuum-processing compartment 314.

Figure 6:
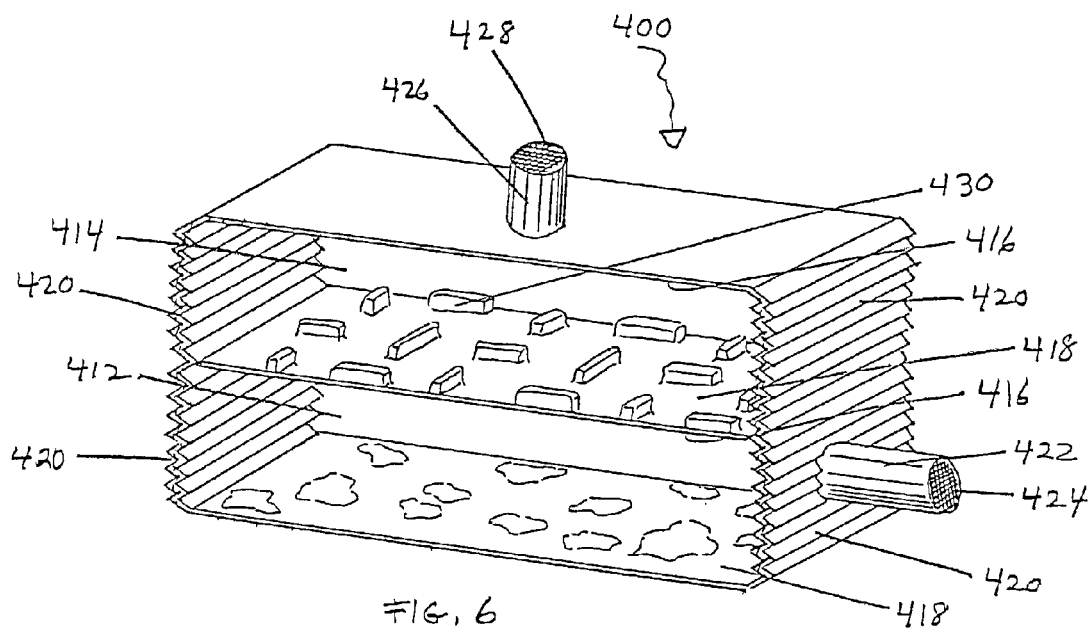
FIG. 6 is a top perspective view, partially in section, of another embodiment of the present invention.

FIG. 6 is an embodiment of a fully collapsible closed container 400 that uses raised crisscrossing plastic bumps to prevent contact between the upper and lower faces 416, 418 of the vacuum-processing compartment 414. The collapsible closed container 400 contains a cavity therein divided into two compartments: a lyophilization compartment 412 and a vacuum-processing compartment 414. Each compartment 412, 414 is bounded by six walls comprised of an upper face 416, a lower face 418, and four lateral faces 420. The upper face 416 of the lyophilization compartment 412 is fabricated entirely or in part with a flexible controlled pore membrane with hydrophobic surfaces, and the four lateral faces 420 are fabricated with a flexible material that is capable of compression under vacuum pressure and of maintaining a barrier between an internal vacuum and the external atmosphere. An access port 422 is located on a lateral face 420 of the lyophilization compartment 412 and is sealed with a microporous hydrophobic membrane barrier 424 to maintain sterility. The upper face 416 of the lyophilization compartment 412 and the lower face 418 of the vacuum-processing compartment 414 serve as a common wall between the lyophilization compartment 412 and the vacuum-processing compartment 414. The upper face 416 of the vacuum-processing compartment 414 and the lower face 418 of the lyophilization compartment 412 are fabricated with a rigid material as described above. The lateral faces 420 of the vacuum-processing compartment 414 are fabricated with a flexible material as described above. The vacuum-processing compartment 414 contains an exit port 426 therein and is sealed with a barrier 428 to maintain sterility. A raised internal restraint 430, composed of a pattern of crisscrossing plastic "bumps," is attached to the lower face 418 of the distal vacuum-processing compartment 414.

FIG. 7 is an embodiment of a semi-collapsible closed container 500, in which the cavity therein is divided into three compartments: a central, lyophilization compartment 512 and two distal vacuum-processing compartments 514. Each compartment 512, 514 is bounded by six walls comprised of an upper face 516, a lower face 518, and four lateral faces 520. The upper face 516 and lower face 518 of the central lyophilization compartment 512 are fabricated entirely or in part with a flexible controlled pore membrane with hydrophobic surfaces and the four lateral faces 520 are fabricated with a flexible material. An access port 522 is located on a lateral face 520 of the central lyophilization compartment 512 and is sealed with a microporous hydrophobic membrane barrier 524 to maintain sterility. The upper face 516 and lower face 518 of the central lyophilization compartment 512, the lower face 518 of the first distal vacuum-processing compartment 514, and the upper face 516 of the second distal vacuum-processing compartment 514 serve as a common wall between the first and second distal vacuum-processing compartments 514 and the central lyophilization compartment 512. The lateral faces 520 of the distal vacuum-processing compartments 514, the upper face 516 of the first distal vacuum-processing compartment 514, and the lower face 518 of the second distal vacuum-processing compartment 514 are fabricated with a rigid material as described above. Each distal vacuum-processing compartment 512, 514 contains an exit port 526 therein and is sealed with a barrier 528 to maintain sterility. Each exit port 526 is connected to a vacuum and condenser system (not shown).

Figure 8:
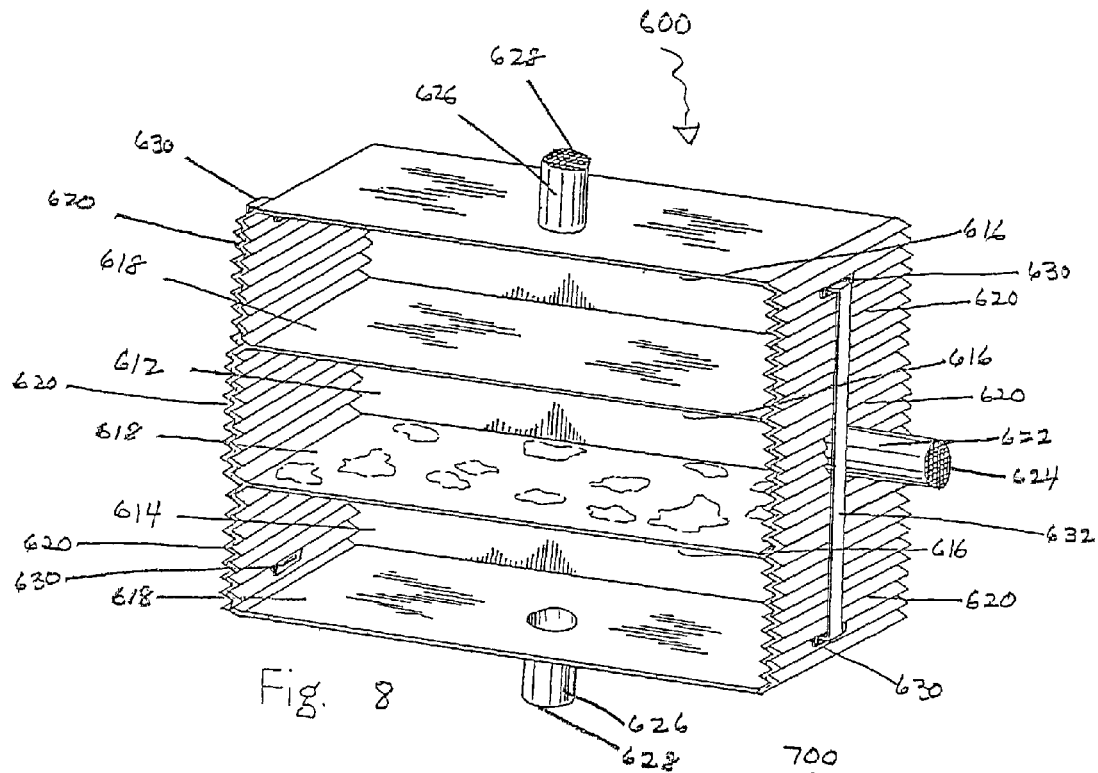
FIG. 8 is a top perspective view, partially in section, of another embodiment of the present.

FIG. 8 is an embodiment of a fully collapsible integrated three-compartment container 600 having two external restraints 632. The container 600 has a cavity therein comprised of a central lyophilization compartment 612 and two distal vacuum-processing compartments 614. Each compartment 612, 614 is bounded by six walls comprised of an upper face 616, a lower face 618, and four lateral faces 620. The upper face 616 and lower face 618 of the central lyophilization compartment 612 are fabricated entirely or in part with a flexible controlled pore membrane with hydrophobic surfaces and the four lateral faces 620 are fabricated with a flexible material. An access port 622 is located on a lateral face 620 of the central lyophilization compartment 612 and is sealed with a microporous hydrophobic membrane barrier 624 to maintain sterility. The upper face 616 and lower face 618 of the central lyophilization compartment 612, the lower face 618 of the first distal vacuum-processing compartment 614, and the upper face 616 of the second distal vacuum-processing compartment 614 serve as a common wall between the first and second distal vacuum-processing compartments 614 and the central lyophilization compartment 612. The lateral faces 620 of the distal vacuum-processing compartments 614, the upper face 616 of the first distal vacuum-processing compartment 614, and the lower face 618 of the second distal vacuum-processing compartment 614 are fabricated with a rigid material as described above. Each distal vacuum-processing compartment 614 contains an exit port 626 therein and is sealed with a barrier 628 to maintain sterility. Each exit port 626 is connected to a vacuum and condenser system (not shown). The outside of each lateral face 620 of the distal vacuum-processing compartments 614 has a tabular structure 630 affixed thereto capable of attaching reversibly to a mechanical external restraint 632 that provides mechanical strength sufficient to retain the distal vacuum-processing compartments 614 from collapse under the vacuum pressure. After lyophilization, the mechanical restraints 632 can be released allowing the container 600 to compress to a minimal volume for storage or transport.

Figure 9:
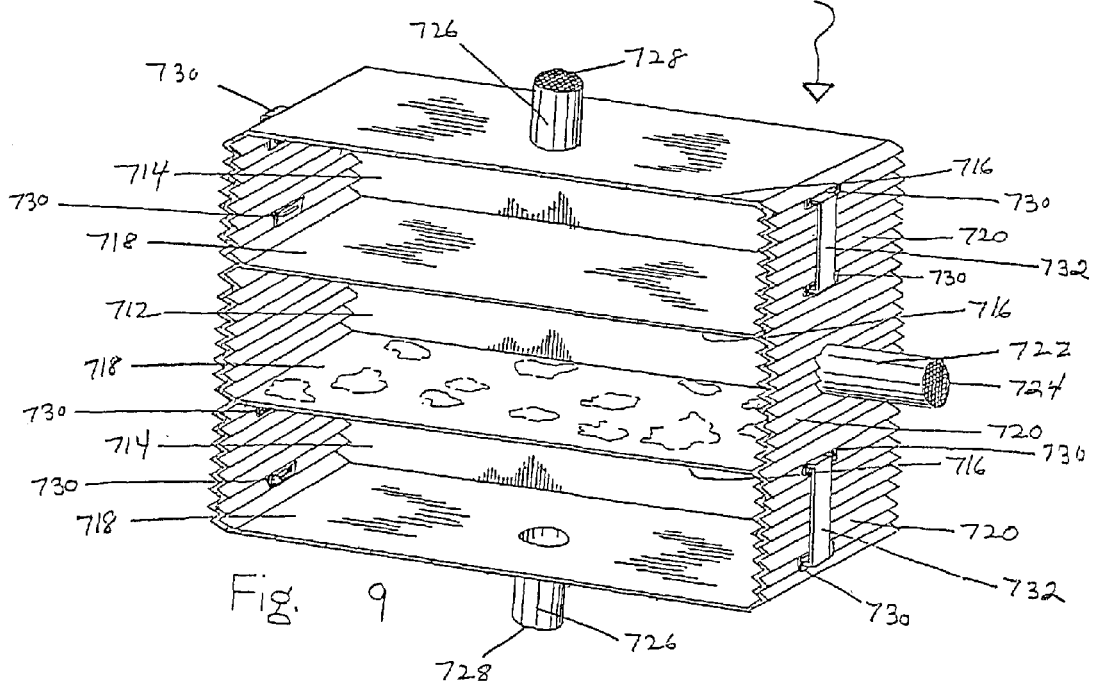
FIG. 9 is a top perspective view, partially in section, of another embodiment of the present invention.

FIG. 9 is an embodiment of a fully collapsible integrated three-compartment container 700 having four external restraints 732. The container 700 has a cavity therein comprised of a lyophilization compartment 712 and two distal vacuum-processing compartments 714. Each compartment 712, 714 is bounded by six walls comprised of an upper face 716, a lower face 718, and four lateral faces 720. The upper face 716 and the lower face 718 of the central lyophilization compartment 712 are fabricated entirely or in part with a flexible controlled pore membrane with hydrophobic surfaces and the four lateral faces 720 are fabricated with a flexible material. An access port 722 is located on a lateral face 720 of the central lyophilization compartment 712 and is sealed with a microporous hydrophobic membrane barrier 724 to maintain sterility. The upper face 716 and the lower face 718 of the central lyophilization compartment 712, the lower face 718 of the first distal vacuum-processing compartment 714, and the upper face 716 of the second distal vacuum-processing compartment 714 serve as a common wall between the first and second distal vacuum-processing compartments 714 and the central lyophilization compartment 712. The lateral faces 720 of the distal vacuum-processing compartments 714, the upper face 716 of the first distal vacuum-processing compartment 714, and the lower face 718 of the second distal vacuum-processing compartment 714 are fabricated with a rigid material as described above. Each distal vacuum-processing compartment 714 contains an exit port 726 therein and is sealed with a barrier 728 to maintain sterility. Each exit port 726 is connected to a vacuum and condenser system (not shown). The outside of each lateral face 720 of each distal vacuum-processing compartment 714 has affixed thereto two tabular structures 730. Each pair of tabular structures 730 is capable of attaching reversibly at its end to a mechanical restraint 732 that provides mechanical strength sufficient to retain the distal vacuum-processing compartments 714 from collapse under the vacuum pressure.

Figure 10:
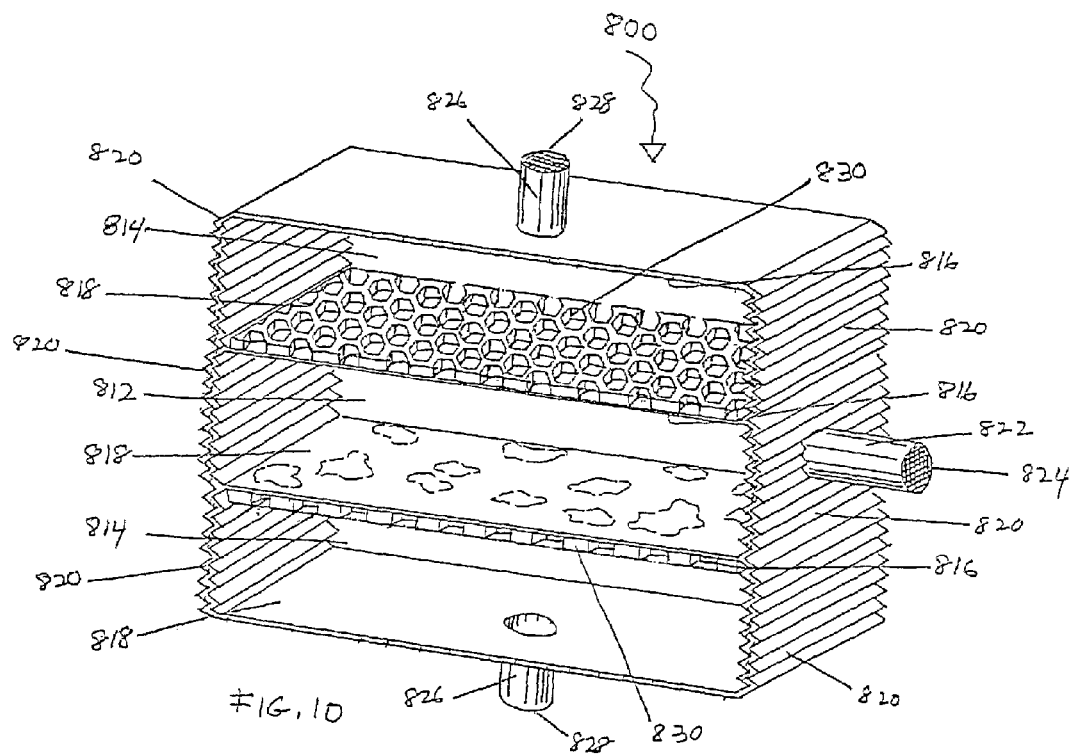
FIG. 10 is a top perspective view, partially in section, of another embodiment of the present invention.

FIG. 10 is an embodiment of a fully collapsible integrated three-compartment container 800 having an internal restraint 830 that can be fabricated of a honeycomb-like open cell plastic structure. The container 800 has a cavity therein comprised of a lyophilization compartment 812 and two distal vacuum-processing compartments 814. Each compartment 812, 814 is bounded by six walls comprised of an upper face 816, a lower face 818, and four lateral faces 820. The upper face 816 and the lower face 818 of the central lyophilization compartment 812 are fabricated entirely or in part with a flexible controlled pore membrane with hydrophobic surfaces, and the four lateral faces 820 are fabricated with a flexible material. An access port 822 is located on a lateral face 820 of the central, lyophilization compartment 812 and is sealed with a microporous hydrophobic membrane barrier 824 to maintain sterility. The upper face 816 and the lower face 818 of the central lyophilization compartment 812, the lower face 818 of the first distal vacuum-processing compartment 814, and the upper face 816 of the second distal vacuum-processing compartment 814 serve as a common wall between the first and second distal vacuum-processing compartments 814 and the central lyophilization compartment 812. The lateral faces 820 of the distal vacuum-processing compartments 814, the upper face 816 of the first distal vacuum-processing compartment 814, and the lower face 818 of the second distal vacuum-processing compartment 814 are fabricated with a rigid material as described above. Each distal vacuum-processing compartment 814 contains an exit port 826 therein and is sealed with a barrier 828 to maintain sterility. Each exit port 826 is connected to a vacuum and condenser system (not shown). One internal restraint 830 is attached to the lower face 818 of the first distal vacuum-processing compartment 814, and another internal restraint 830 is attached to the upper face 816 of the second distal vacuum-processing compartment 814.

Figure 11:
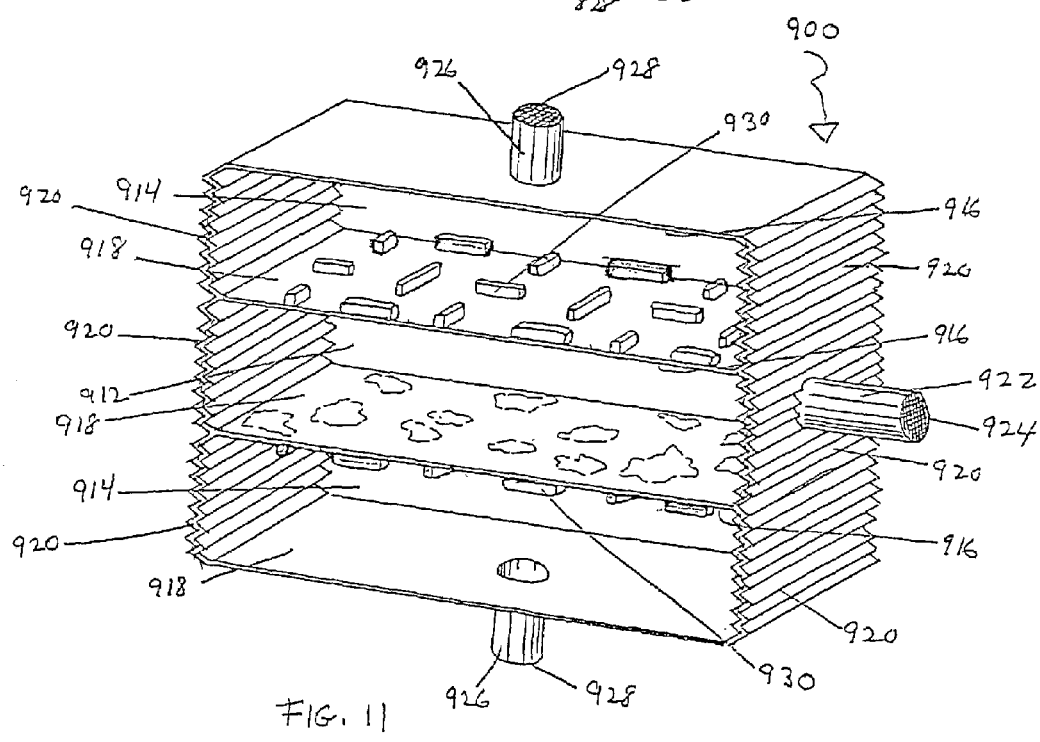
FIG. 11 is a top perspective view, partially in section, of another embodiment of the present invention.

FIG. 11 is an embodiment of a fully collapsible integrated three-compartment container 900 having an internal restraint 930 made of raised crisscrossing plastic "bumps." The container 900 has a cavity therein comprised of a lyophilization compartment 912 and two distal vacuum-processing compartments 914. Each compartment 912, 914 is bounded by six walls comprised of an upper face 916, a lower face 918, and four lateral faces 920. The upper face 916 and the lower face 918 of the central lyophilization compartment 912 are fabricated entirely or in part with a flexible controlled pore membrane with hydrophobic surfaces and the four lateral faces 920 are fabricated with a flexible material. An access port 922 is located on a lateral face 920 of the central lyophilization compartment 912 and is sealed with a microporous hydrophobic membrane barrier 924 to maintain sterility. The upper face 916 and the lower face 918 of the central lyophilization compartment 912, the lower face 918 of the first distal vacuum-processing compartment 914, and the upper face 916 of the second distal vacuum-processing compartment 914 serve as a common wall between the first and second distal vacuum-processing compartments 914 and the central lyophilization compartment 912. The lateral faces 920 of the distal vacuum-processing compartments 914, the upper face 916 of the first distal vacuum-processing compartment 914, and the lower face 918 of the second distal vacuum-processing compartment 914 are fabricated with a rigid material as described above. Each distal vacuum-processing compartment 914 contains an exit port 926 therein and is sealed with a barrier 928 to maintain sterility. Each exit port 926 is connected to a vacuum and condenser system (not shown). One raised internal restraint 930 lies on top of the lower face 918 of the distal vacuum-processing compartment 914 and can be composed of a pattern of crisscrossing plastic "bumps."

FIG. 12 is an embodiment of a non-collapsible closed container 1000 in which the cavity therein is divided into three compartments: a central lyophilization compartment 1012 and two distal vacuum-processing compartments 1014. Each compartment 1012, 1014 is bounded by six walls comprised of an upper face 1016, a lower face 1018, and four lateral faces 1020. The upper face 1016 and the lower face 1018 of the central lyophilization compartment 1012 are fabricated entirely or in part with a flexible controlled pore membrane with hydrophobic surfaces. An access port 1022 is located on a lateral face 1020 of the central lyophilization compartment 1012 and is sealed with a microporous hydrophobic membrane barrier 1024 to maintain sterility. The upper face 1016 and the lower face 1018 of the central lyophilization compartment 1012, the lower face 1018 of the first distal vacuum-processing compartment 1014, and the upper face 1016 of the second distal vacuum-processing compartment 1014 serve as a common wall between the first and second distal vacuum-processing compartments 1014 and the central lyophilization compartment 1012. The lateral faces 1020 of the three compartments 1012 and 1014, the upper face 1016 of the first distal vacuum-processing compartment 1014, and the lower face 1018 of the second distal vacuum-processing compartment 1014 are fabricated with a rigid material as described above. Each distal vacuum-processing compartment 1014 contains an exit port 1026 therein and is sealed with a barrier 1028 to maintain sterility. Each exit port 1026 is connected to a vacuum and condenser system (not shown).

Depending on the needs of the user, additional sample processing steps might be needed before sample use. For example, successful lyophilization of cells often requires high concentrations of materials, such as mannitol or trehalose, for their cryosurvival. It often would be useful to remove those low molecular weight materials from the desired cells before use.

To accomplish this, a further embodiment of the present invention is illustrated in FIG. 13 in which a semi-collapsible integrated closed container 1100 is comprised of five compartments: a central lyophilization compartment 1112, two distal vacuum-processing compartments 1114, and two external compartments 1134. Each compartment 1112, 1114, 1134 is bounded by six walls comprised of an upper face 1116, a lower face 1118, and four lateral faces 1120. The upper face 1116 and the lower face 1118 of the central lyophilization compartment 1012 are fabricated entirely or in part with a flexible controlled pore membrane with hydrophobic surfaces and the four lateral faces 1120 are fabricated with a flexible material. The upper face 1116 and the lower face 1118 of the central lyophilization compartment 1112, the lower face 1118 of the first distal vacuum-processing compartment 1114, and the upper face 1116 of the second distal vacuum-processing compartment 1114 serve as a common wall between the first and second distal vacuum-processing compartments 1114 and the central lyophilization compartment 1112. The lateral faces 1120 of the distal vacuum-processing compartments 1114, the upper face 1116 of the first distal vacuum-processing compartment 1114 and the external compartments 1134, and the lower face 1118 of the second distal vacuum-processing compartment 1114 and the external compartments 1134 are fabricated with a rigid material as described above. Two lateral faces 1120 of the central lyophilization compartment 1112 are fabricated with a flexible material. An access port 1122 is located on the outer lateral faces 1120 of the external compartments 1134 and is sealed with a microporous hydrophobic membrane barrier 1124 to maintain sterility. The inner lateral faces 1120 of the external compartments 1134 serve as common walls between the external compartments 1134 and the two lateral faces 1120 of the central lyophilization compartment 1112 and are fabricated with a porous surface containing pores which are initially filled with an erodible or otherwise removable pore plugging substance as further described in U.S. Pat. Nos. 5,026,342 and 5,261,870, incorporated herein by reference.

Many simple variations of this invention will be apparent to those skilled in the art. For example, increasing or decreasing the number of vacuum-processing compartments and alteration of the hydrophobic membrane materials will affect the rate of water removal and change the surface area through which water vapor will pass. A wide variety of materials can be used for construction of the container, allowing fabrication of unique containers with exceptional pliability, low weight, chemical reactivity, enhanced compatibility with biological materials, optical properties, and other physical properties. Depending upon the needs of the user, for instance, if storage and transport of the biological material is not required, the outer walls of the container can be fabricated with a rigid material instead of more pliable materials, thus eliminating the use of mechanical restraints during lyophilization.

EXAMPLE 1

Lyophilization and Storage of Blood Plasma Under Vacuum or Inert Gas Conditions

The lower compartment is filled via its access port with 15 ml of bovine blood plasma recovered from the blood fractionation process, after which the access port is sealed. External mechanical restraints are attached to tabs located on the exterior surfaces of the compartments in order to provide mechanical strength sufficient to retain the compartments from collapse under the vacuum pressure. The filled lower compartment is cooled to −20° C. or colder to freeze the water within. The exit port of the upper compartment, protected by barriers to assure maintenance of sterility, is connected to a vacuum and condenser system (not shown), and the water is removed as vapor without thawing the blood plasma in the lower compartment. After the water is removed, the exit port from the upper compartment to the vacuum is sealed. Alternatively, the lower compartment can be filled with inert gases according to the needs of the user while under vacuum. The external restraints are then released, thus allowing the compartments to collapse to a minimal volume. The sample is stored under conditions suitable for blood plasma. When appropriate, the lyophilized blood plasma in the lower compartment is rehydrated by the addition of sterile water via the access port, in which the vacuum therein allows "self filling" to the maximum volume of the compartment.

EXAMPLE 2

Container for Lyophilization, Storage, and Processing of Cell Suspensions After Rehydration The lower compartment is filled via its access port with a cell suspension containing cryoprotectant materials that are essential for cellular survival during lyophilization, such as mannitol or trehalose, after which the access port is sealed. External mechanical restraints are attached to tabs located on the exterior surfaces of the compartments in order to provide mechanical strength sufficient to retain the compartments from collapse under the vacuum pressure. The filled lower compartment is cooled to −20° C. or colder to freeze the water within. The exit port of the upper compartment, protected by barriers to assure maintenance of sterility, is connected to a vacuum and condenser system (not shown), and the water is removed as vapor without thawing the blood plasma in the lower compartment. After the water is removed, the exit port from the upper compartment to the vacuum is sealed. The external restraints are then released, thus allowing the compartments to collapse to a minimal volume. The sample is stored under conditions suitable for the specific cell suspension. When appropriate, the lyophilized cell suspension in the lower compartment is rehydrated by the addition of sterile water or buffer medium via the access port in which the vacuum therein allows "self filling" to the maximum volume of the compartment. In order to remove the cryoprotectant materials after storage and before use, the external compartments are activated and used as further described in U.S. Pat. No. 6,065,294, incorporated herein by reference.

Although the invention has been described with particularity above, the invention is only to be considered limited insofar as is set forth in the accompanying claims.

The invention claimed is:

1. An integrated container to lyophilize, store, transport, rehydrate, and process biological materials, comprising:
   a) a closed construct, said closed construct defining a cavity therein, said cavity further comprising a lyophilization compartment having an upper face and a lower face and four lateral faces, wherein said upper face is fabricated with a first flexible controlled pore membrane with hydrophobic surfaces that allows passage of water in a vapor but not liquid state, said lower face is fabricated with a second flexible controlled pore membrane, and said lateral faces are fabricated with a rigid material, a flexible material, or any combination thereof;
   b) one of four said lateral faces having an access port therein to allow entry or removal of biological or other materials and water, said access port having a barrier to maintain sterility;
   c) a first distal vacuum-processing compartment and a second distal vacuum-processing compartment, said first distal vacuum-processing compartment having an upper face and four lateral faces, said first controlled pore membrane of said lyophilization compartment serving as a lower face of said first distal vacuum-processing compartment and as a common wall between said lyophilization compartment and said first distal vacuum-processing compartment, said second distal vacuum-processing compartment having a lower face and four lateral faces, said second controlled pore membrane of said lyophilization compartment serving as an upper face of said second distal vacuum-processing compartment and as a common wall between said lyophilization compartment and said second distal vacuum-processing compartment, and said upper face of said first distal vacuum-processing compartment, said lower face of said second distal vacuum-processing compartment, said lateral faces of said distal vacuum-processing compartments being fabricated with a rigid material, a flexible material or any combination thereof, wherein said upper face of said first distal vacuum-processing compartment and said lower face of said second distal vacuum-processing compartment has an exit port therein with a barrier to maintain sterility, said exit ports connected to a vacuum and condenser system suitable for aseptic removal of water vapor; and
   (d) a first external compartment and a second external compartment, said external compartments each having an upper face, a lower face, and four lateral faces, said upper face, said lower face, and a first and second lateral face being fabricated with a rigid material, an outer lateral face being fabricated with a flexible material, and an inner lateral face being fabricated from a porous surface having at least one pore formed therein, said pore being filled with an erodible substance, each said inner lateral face serving as a common wall between said external compartment and said lyophilization compartment, wherein each said outer lateral face of each said external compartment contains an access port therein.

2. The integrated container according to claim 1, wherein said lateral faces of said distal vacuum-processing compartments are fabricated with a flexible material capable of maintaining a barrier between an internal vacuum and the external atmosphere.

3. The integrated container according to claim 2, wherein each lateral face of said distal vacuum-processing compartment contains a tabular structure that attaches to one of two ends of an external mechanical restraint, said restraints providing mechanical strength sufficient to retain said vacuum-processing compartment from collapse under vacuum pressure, whereby said restraints are released after lyophilization to allow collapse of said distal vacuum-processing compartments to a minimal volume.

4. The integrated container according to claim 2, wherein each lateral face of said distal vacuum-processing compartment contains two tabular structures that attach to one of two ends of an external mechanical restraint, said restraints providing mechanical strength sufficient to retain said vacuum-processing compartments from collapse under vacuum pressure, whereby said restraints are released after lyophilization to allow collapse of said distal vacuum-processing compartments to a minimal volume.

5. The integrated container according to claim 2, wherein an internal mechanical restraint, composed of a mesh is attached to said lower face of said first distal vacuum-processing compartment and to said upper face of said second distal vacuum-processing compartment, whereby mechanical strength is provided sufficient to prevent said upper face of said first distal vacuum-processing compartment and said lower face of said second distal vacuum-processing compartment from coming in contact with said flexible controlled pore membrane.

6. The integrated container according to claim 2, wherein an internal mechanical restraint composed of a plurality of crisscrossing raised plastic "bumps" is attached to said lower face of said first distal vacuum-processing compartment and said upper face of said second distal vacuum-processing compartment, whereby mechanical strength is provided sufficient to prevent said upper face of said first distal vacuum-processing compartment and said lower face of said second distal vacuum-processing compartment from coming in contact with said flexible controlled pore membrane.

7. The integrated container according to claim 1, wherein said lateral faces of said lyophilization compartment are fabricated with a rigid material.

* * * * *